US008772519B2

(12) United States Patent
Hill et al.

(10) Patent No.: US 8,772,519 B2
(45) Date of Patent: Jul. 8, 2014

(54) PROCESS FOR PREPARING MONO-ALLYL-FUNCTIONALIZED DIALKYLPHOSPHINIC ACIDS, SALTS AND ESTERS THEREOF WITH ALLYLIC COMPOUNDS, AND THE USE THEREOF

(75) Inventors: Michael Hill, Cologne (DE); Werner Krause, Huerth (DE); Martin Sicken, Cologne (DE)

(73) Assignee: Clariant Finance (BVI) Limited, Tortola (VG)

( * ) Notice: Subject to any disclaimer, the term of this patent is extended or adjusted under 35 U.S.C. 154(b) by 325 days.

(21) Appl. No.: 13/127,110

(22) PCT Filed: Oct. 6, 2009

(86) PCT No.: PCT/EP2009/007135
§ 371 (c)(1),
(2), (4) Date: May 2, 2011

(87) PCT Pub. No.: WO2010/054722
PCT Pub. Date: May 20, 2010

(65) Prior Publication Data
US 2011/0213080 A1 Sep. 1, 2011

(30) Foreign Application Priority Data
Nov. 11, 2008 (DE) .......................... 10 2008 056 691

(51) Int. Cl.
C07F 9/30 (2006.01)
C07F 9/32 (2006.01)
C07F 5/06 (2006.01)

(52) U.S. Cl.
USPC .................... 556/20; 562/8; 558/87; 556/174

(58) Field of Classification Search
USPC ............................ 556/20, 174; 562/8; 558/87
See application file for complete search history.

(56) References Cited

U.S. PATENT DOCUMENTS

| 3,345,432 A | 10/1967 | Gillham et al. |
| 3,784,638 A | 1/1974 | Lambert |
| 3,875,263 A | 4/1975 | Herwig et al. |
| 3,939,050 A | 2/1976 | Kleiner et al. |
| 3,941,752 A | 3/1976 | Kleiner et al. |
| 3,962,194 A | 6/1976 | Bollert et al. |
| 4,001,352 A | 1/1977 | Kleiner et al. |
| 4,035,343 A | 7/1977 | Bollert et al. |
| 4,069,245 A | 1/1978 | Dursch et al. |
| 4,069,247 A | 1/1978 | Kleiner |
| 4,079,049 A | 3/1978 | Ramsey et al. |
| 4,168,267 A | 9/1979 | Petrillo |
| 4,235,991 A | 11/1980 | Digiacomo |
| 4,337,201 A | 6/1982 | Petrillo |
| 4,374,131 A | 2/1983 | Petrillo |
| 4,381,297 A | 4/1983 | Karanewsky et al. |
| 4,427,665 A | 1/1984 | Karanewsky et al. |
| 4,555,506 A | 11/1985 | Karanewsky et al. |
| 4,594,199 A | 6/1986 | Thottathil et al. |
| 4,602,092 A | 7/1986 | Thottathil et al. |
| 4,634,689 A | 1/1987 | Witkowski et al. |
| 5,013,863 A | 5/1991 | Baylis et al. |
| 5,153,347 A | 10/1992 | Lloyd |
| 5,190,934 A | 3/1993 | Mickel et al. |
| 5,229,379 A | 7/1993 | Marescaux et al. |
| 5,391,743 A | 2/1995 | Ebitino et al. |
| 5,407,922 A | 4/1995 | Marescaux et al. |
| 5,545,631 A | 8/1996 | Marescaux |
| 5,739,123 A | 4/1998 | Norcini et al. |
| 5,780,534 A | 7/1998 | Kleiner et al. |
| 5,973,194 A * | 10/1999 | Weferling et al. ............. 562/8 |
| 6,011,172 A * | 1/2000 | Weferling et al. ............. 562/8 |
| 6,013,707 A | 1/2000 | Kleiner et al. |

(Continued)

FOREIGN PATENT DOCUMENTS

| AT | 243952 | 12/1965 |
| DE | 1494922 | 6/1969 |

(Continued)

OTHER PUBLICATIONS

Valiaeva, Phosphinc Acid Pseudopeptides Analogous to Glutamyl-gamma-glutamate: Journal of Organic Chemistry 2001, No. 66 pp. 5146-5154.*
PCT International Search Report for PCT/EP2009/007145, mailed Jan. 25, 2010.
English Translation of the PCT International Preliminary Report on Patentability PCT/EP2009/007145 mailed Jun. 30, 2011.
English abstract for JP 05230085, Sep. 7, 1993.
Russian Journal of General Chemistry (translation of Zhurnal Obschchei Khimii), 74(6) pp. 864-872; XP002561442 (2004).
PCT International Search Report for PCT/EP2009/007123, mailed Jan. 29, 2010.
English Translation of the PCT International Preliminary Report on Patentability PCT/EP2009/0071123 mailed May 19, 2011.

(Continued)

*Primary Examiner* — Porfirio Nazario Gonzalez
(74) *Attorney, Agent, or Firm* — Anthony A. Bisulca

(57) ABSTRACT

The invention relates to a process for preparing mono-allyl-functionalized dialkylphosphinic acids, esters and salts with allylic compounds, characterized in that a) a phosphinic acid source (I) is reacted with olefins (IV) in the presence of a catalyst A to give an alkylphosphonous acid, or salt or ester thereof (II), b) the alkylphosphonous acid, or salt or ester thereof (II) thus formed is reacted with allylic compounds of the formula (V) in the presence of a catalyst B and of a base to give a mono-allyl-functionalized dialkylphosphinic acid derivative (III), where $R^1$, $R^2$, $R^3$, $R^4$, $R^5$, $R^6$, $R^7$, $R^8$, $R^9$ are the same or different and are each independently, inter alia, H, $C_1$-$C_{18}$-alkyl, $C_6$-$C_{18}$-aryl, $C_6$-$C_{18}$-aralkyl, $C_6$-$C_{18}$-alkylaryl, and X is H, $C_1$-$C_{18}$-alkyl, $C_6$-$C_{18}$-aryl, $C_6$-$C_{18}$-aralkyl, $C_6$-$C_{18}$-alkylaryl, Mg, Ca, Al, Sb, Sn, Ge, Ti, Fe, Zr, Zn, Ce, Bi, Sr, Mn, Cu, Ni, Li, Na, K and/or a protonated nitrogen base, and the catalysts A and B are transition metals and/or transition metal compounds and/or catalyst systems which are composed of a transition metal and/or a transition metal compound and at least one ligand.

11 Claims, No Drawings

(56) References Cited

U.S. PATENT DOCUMENTS

| | | | |
|---|---|---|---|
| 6,090,968 A | 7/2000 | Horold et al. | |
| 6,214,812 B1 | 4/2001 | Karpeisky | |
| 6,300,516 B1* | 10/2001 | Weferling et al. | 562/8 |
| 6,329,544 B1* | 12/2001 | Weferling et al. | 562/8 |
| 6,355,832 B1* | 3/2002 | Weferling et al. | 562/8 |
| 6,384,022 B1 | 5/2002 | Jackson et al. | |
| 6,569,974 B1 | 5/2003 | Sicken et al. | |
| 6,727,335 B2 | 4/2004 | Sicken et al. | |
| 6,855,757 B2 | 2/2005 | Horold et al. | |
| 7,446,140 B2 | 11/2008 | Bauer | |
| 7,473,794 B2 | 1/2009 | Wehner et al. | |
| 7,485,745 B2 | 2/2009 | Maas et al. | |
| 7,749,985 B2 | 7/2010 | Gallop et al. | |
| 7,829,736 B2 | 11/2010 | Wehner et al. | |
| 8,084,518 B2 | 12/2011 | Bauer | |
| 8,097,753 B2 | 1/2012 | Maas et al. | |
| 2002/0187977 A1 | 12/2002 | Pearlman et al. | |
| 2003/0171466 A1 | 9/2003 | Horold et al. | |
| 2003/0216533 A1 | 11/2003 | Sicken et al. | |
| 2005/0187196 A1 | 8/2005 | Madrid et al. | |
| 2006/0084734 A1 | 4/2006 | Bauer et al. | |
| 2006/0194973 A1 | 8/2006 | Gainer et al. | |
| 2006/0264654 A1 | 11/2006 | Wehner | |
| 2007/0210288 A1 | 9/2007 | Maas et al. | |
| 2007/0213436 A1 | 9/2007 | Maas et al. | |
| 2007/0213563 A1 | 9/2007 | Maas et al. | |
| 2008/0183009 A1 | 7/2008 | Wehner et al. | |
| 2008/0214708 A1 | 9/2008 | Bauer et al. | |
| 2009/0286759 A1 | 11/2009 | Gallop et al. | |
| 2010/0093239 A1 | 4/2010 | Bauer et al. | |
| 2011/0201732 A1 | 8/2011 | Hill et al. | |
| 2011/0201733 A1 | 8/2011 | Hill et al. | |
| 2011/0213052 A1* | 9/2011 | Hill et al. | 523/400 |
| 2011/0213059 A1* | 9/2011 | Hill et al. | 524/133 |
| 2011/0213060 A1 | 9/2011 | Hill et al. | |
| 2011/0213061 A1* | 9/2011 | Hill et al. | 524/135 |
| 2011/0213062 A1* | 9/2011 | Hill et al. | 524/135 |
| 2011/0213078 A1* | 9/2011 | Hill et al. | 524/605 |
| 2011/0213079 A1 | 9/2011 | Hill et al. | |
| 2011/0224339 A1* | 9/2011 | Hill et al. | 524/133 |
| 2011/0224340 A1* | 9/2011 | Hill et al. | 524/139 |
| 2011/0234340 A1 | 9/2011 | Hill et al. | |
| 2011/0237720 A1* | 9/2011 | Hill et al. | 524/133 |
| 2011/0237721 A1* | 9/2011 | Hill et al. | 524/133 |
| 2011/0237722 A1* | 9/2011 | Hill et al. | 524/133 |
| 2011/0245385 A1 | 10/2011 | Hill et al. | |
| 2011/0245386 A1 | 10/2011 | Hill et al. | |
| 2011/0251310 A1 | 10/2011 | Hill et al. | |
| 2011/0251312 A1 | 10/2011 | Hill et al. | |
| 2011/0251314 A1 | 10/2011 | Hill et al. | |
| 2011/0251315 A1 | 10/2011 | Hill et al. | |
| 2011/0275744 A1* | 11/2011 | Hill et al. | 524/133 |
| 2011/0281983 A1* | 11/2011 | Hill et al. | 524/135 |
| 2012/0064790 A1 | 3/2012 | Bauer et al. | |

FOREIGN PATENT DOCUMENTS

| | | |
|---|---|---|
| DE | 2236036 | 2/1974 |
| DE | 2236037 | 2/1974 |
| DE | 2302523 | 2/1974 |
| DE | 2344332 | 3/1975 |
| DE | 2441878 | 3/1976 |
| DE | 2623775 | 12/1976 |
| DE | 2942781 | 4/1980 |
| DE | 10153780 | 11/2002 |
| DE | 19912920 | 9/2009 |
| EP | 00858391 | 8/1983 |
| EP | 0319482 | 6/1989 |
| EP | 0463560 | 1/1992 |
| EP | 0699708 | 3/1996 |
| EP | 0906915 | 4/1999 |
| EP | 0969008 | 1/2000 |
| EP | 1203770 | 5/2002 |
| EP | 1369422 | 12/2003 |
| EP | 1607400 | 12/2005 |
| EP | 1693403 | 8/2006 |
| EP | 1832594 | 9/2007 |
| EP | 1832595 | 9/2007 |
| EP | 1832596 | 9/2007 |
| EP | 1905776 | 4/2008 |
| GB | 1045684 | 10/1966 |
| JP | 05230085 | 9/1993 |
| WO | WO 99/28327 | 6/1999 |
| WO | WO 01/42252 | 6/2001 |
| WO | WO 0157050 | 8/2001 |
| WO | WO 02/100871 | 12/2002 |
| WO | WO 2005/014604 | 2/2005 |
| WO | WO 2005/032494 | 4/2005 |
| WO | WO 2005/044830 | 5/2005 |
| WO | WO 2007/052169 | 5/2007 |
| WO | WO 2008/033572 | 3/2008 |
| WO | WO 2008/043499 | 4/2008 |

OTHER PUBLICATIONS

Montchamp; "Recent advances in phosphorus-carbon bond formation: synthesis of H-phosphinic acid derivatives from hypophosphus compounds" Journal of Organometallic Chemistry Elsevier-Sequoua S.A. Lausanne, CH, vol. 690; pp. 2388-2406; XP004877374 (May 16, 2005).

Sylvine Deprele et al. "Palladium-Catalyzed Hydrophosphinylation of Alkenes and Alkynes;" Journal of the American Chemical Society, American Chemical Society, Washington DC, US vol. 124, No. 32 p. 9387, XP002500862 (Jan. 1, 2002).

Bravo-Altamirano et al.: "A Novel Approach to Phosphinic Acids from Hypophosphorus Acid;" Tetrahedron Letters, Elsevier, Amsterdam, NL vol. 48, No. 33, pp. 5755-5759, XP022163552 (Jul. 19, 2007).

Sylvine Deprele et al.: "Environmentally Benign Synthesis of H-Phosphinic Acids Using a Water Tolerant, Recyclable Polymer-Supported Catalyst;" Organic Letters, American Chemical Society, US, vol. 6, No. 21, pp. 3805-3808 XP002500861 (Jan. 1, 2004).

Patrice Ribiere et al: " NiCL2-Catalyzed Hydrophosphinylation;" Journal of Organic Chemistry, American Chemical Society, Easton, US, vol. 70, No. 10, pp. 4064-4072, XP002530191 (Jan. 1, 2005).

Coudray L. et al.: "Allylic Phosphinates via Pd-Catalyzed Allylation of H-Phosphinic Acids with Allylic Alcohols;" Organic letters, vol. 10, No. 6, pp. 1123-1126 XP002561368 (Feb. 21, 2008).

Mastalerz: Synthesis of some ethylene-(P,P'-Dialkyl)-Diphosphic Acids as new Potential Antimetabolites of Succinic Acid; Roczniki Chemii Ann. Soc. Chim. Polonorum, vol. 38 pp. 61-66 XP 009126234 (1964).

Kurdyumova et al.: "Synthesis of Phosphinic Acids from Hypophosphites I Acrylates as an Unsaturated Component;" Russian Journal of General Chemistry (Translation of Zhurnal Obshchei Khimii (1997), 67(12) pp. 1852-1856 (Apr. 25, 1997).

Houben-Weyl, vol. 1211, pp. 258-259 (Apr. 22, 1963).

Houben-Weyl, vol. 1211, p. 306 (Apr. 22, 1963).

English abstract of Khairullin et al, "Reaction of chlorides of acids of trivalent phosphorus with conjugated systems I. Reaction of ethylphosphonous dichloride with alpha-beta-unstaturated acids" Zh. Obshch. Khimii. 36, pp. 289-296 (1966).

PCT International search report for PCT/EP2009/007124, mailed Feb. 22, 2010.

PCT International Preliminary Report on Patentability for PCT/EP2009/007124, mailed May 19, 2011.

Piotr Majewski: "A New Method for the Preparation of Bis(1-hydroxyalkyl)-phosphinic Acids;" Synthesis, vol. 6, pp. 555-557, XP002558292 (1987).

Hung Kuei Lin et al.: "Competitive inhibition of interfacial catalysis by phospholipase A2: differential interaction of inhibitors with the vesicle interface a controlling factor of inhibitor potency" J. Am. Chem. Soc, vol. 115, No. 10, 1993, pp. 3932-3942 XP009126627 (1993).

Kallinowsky G. et al.: "C13 Nuclear Magnetic Resonance Study of Some Phosphinolipids: Assignments and Conformational Studies;" Magnetic Resonance in Chemistry, vol. 27, No. 7, pp. 647-652 XP002558647 (1989).

(56) References Cited

OTHER PUBLICATIONS

PCT International Search Report for PCT/EP2009/007125, mailed Feb. 22, 2010.
English translation of PCT International Preliminary Report on Patentability for PCT/EP2009/007125, mailed May 19, 2011.
PCT International search report for PCT/EP2009/007126, mailed Sep. 2, 2010.
English translation of PCT International Preliminary Report on Patentability for PCT/EP2009/007126, mailed May 19, 2011.
Froestl W. et al.: "Phosphinic Acid Analogues of Gaba. 2. Selective, Orally Acitive Gabab Antagonists," Journal of Medicinal Chemistry, American Chemical Society, Washington, US, vol. 38, No. 17, pp. 3313-3331, XP000999491 (Jan. 1, 1995).
PCT International Preliminary Report on Patentability for PCT/EP2009/007127, mailed Jan. 18, 2010.
English translation of PCT International Preliminary Report on Patentability for PCT/EP2009/007127, mailed May 19, 2011.
PCT International Preliminary Report on Patentability for PCT/EP2009/007128, mailed Jan. 27, 2010.
English translation of PCT International Preliminary Report on Patentability for PCT/EP2009/007128, mailed May 19, 2011.
PCT International Preliminary Report on Patentability for PCT/EP2009/007129, mailed Feb. 22, 2010.
English translation of PCT International Preliminary Report on Patentability for PCT/EP2009/007129, mailed May 19, 2011.
PCT International Preliminary Report on Patentability for PCT/EP2009/007130, mailed Apr. 29, 2010.
English translation of PCT International Preliminary Report on Patentability for PCT/EP2009/007130, mailed May 19, 2011.
Nifant'ev et al.: "Reactions of acetylenes with hypophosphorous aand phosphous acids;" Journal of General Chemistry USSR Consultants Bureau, New York, NY, US vol. 56 No. 4 pp. 680-688 XP002165520 (Sep. 20, 1986).
English Abstract for DE 2344332, Mar. 27, 1975.
Kabachnik et al.: "Synthesis and properties of some ethylenepiphosphoryl compounds," Russian Chemical Bulletin, vol. 23, No. 10 p. 2205 XP002557075 (1974).
Saratovskikh I. et al.: "Phosphorus-containing Aminocarboxylic Acids: XIV. Synthesis of Analogs of [alpha]-Substituted Glutamic Acid" Russian Journal of General Chemistry Nauka/Interperiodica, Mo, vol. 75, No. 7 pp. 1077-1084 XP019301159 (Jul. 1, 2005).
Chemical Abstracts Service, Columbus, Ohio, US: Gareev et al.: "Stereochemistry of a 1,3-dipolar cycloaddition of diazomethane to alpha-substituted vinylphosphoryl compounds containing a chiral phosphorus atom" XP002567581 (1979).
Chemical Abstracts Service, Columbus, Ohio, US: Raevskii et al. "Electron-donor and acceptor functions of physiologically active and model compounds. V. Calculation of the electron-donor function of phosphoryl oxygen" XP002567582 (1984).
Isabelle Abrunhosa Thomas et al.: "Alkylation of H-Phosphinate Esters under Basic Conditions;" Jounal of Organic Chemistry, American Chemical Society, Easton; US, vol. 72, No. 8 pp. 2851-2856 XP002530192 (Jan. 1, 2007).
Catherine Ruflin et al.: "Tetrakis(trimethylsilyl)hypophosphate P2O2(OTMS)4: Synthesis, reactivity and application as flame retardants;" Heteroatom Chemistry, VCH publishers, Defield Beach, FL, US, vol. 18, No. 7 pp. 721-731 XP009118331 (Nov. 6, 2007).
PCT International Search Report for PCT/EP2009/007131, mailed Feb. 8, 2010.
English translation of the PCT International Preliminary Report on Patentability for PCT/EP2009/007131, mailed May 19, 2011.
PCT International Preliminary Report on Patentability for PCT/EP2009/007132, mailed Feb. 15, 2010.
English translation of PCT International Preliminary Report on Patentability for PCT/EP2009/007132, mailed May 19, 2011.
PCT International Preliminary Report on Patentability for PCT/EP2009/007133, mailed Feb. 3, 2010.
English translation of PCT International Preliminary Report on Patentability for PCT/EP2009/007133, mailed May 19, 2011.

Database Beilstein [Online] Beilstein Institute for Organic Chemistry, Frankfurt-Main, DE; XP002561148, retrived from xfire Database accession No. Reaction ID 198358, abstract (1954).
PCT International Preliminary Report on Patentability for PCT/EP2009/007134, mailed Feb. 18, 2010.
English translation of PCT International Preliminary Report on Patentability for PCT/EP2009/007134, mailed May 19, 2011.
PCT International Preliminary Report on Patentability for PCT/EP2009/007135, mailed Mar. 17, 2010.
English translation of PCT International Preliminary Report on Patentability for PCT/EP2009/007135, mailed May 26, 2011.
Bravo-Altamirano et al.: "Palladium-Catalyzed Reaction of Hypophosphorous Compounds with Allenes, Dienes, and Allylic Electrophiles: Methodology for the Synthesis of Allylic H-Phosphinates" J. Org. Chem., vol. 73, No. 6, pp. 2292-2301 XP002567417 (Feb. 15, 2008).
Nadia Valiaeva et al.: "Phosophinic Acid Pseudopeptides Analogous to Glutamyl-gamma-glutamate: Synthesis and Coupling to Pteroyl Azides Leads to Potent Inhibitors of Folypoly-gamma-glutamate Synthetase;" J. Or. Chem., vol. 66, pp. 5146-5154 XP002567418 (2001).
Yamagishi takehiro et al.: "Stereoselective Synthesis of beta-Amino-alpha-hydroxy(allyl)phosphinates and an Application to the Synthesis of a Building Block for Phosphinyl Peptides" Synlett, No. 9, pp. 1471-1474, XP 002567142 (Jan. 1, 2002).
PCT International Search Report for PCT/EP2009/007136, mailed Mar. 22, 2010.
English translation of the PCT International Preliminary Report on Patentability for PCT/EP2009/007136, mailed Jun. 16, 2011.
Database Beilstein [online] Beilstein Institute for Organic Chemistry, Frankfurt-Main, DE; Database accession No. Reaction ID 101395 XP 002567148 (1956).
PCT International Search Report for PCT/EP2009/007137, mailed Mar. 12, 2010.
English translation of the PCT International Preliminary Report on Patentability for PCT/EP2009/007137, mailed Jun. 16, 2011.
Yamagishi et al.: "Diastereoselective synthesis of beta-substituted alpha-hydroxyphosphinates through hydrophosphinylation of alpha-heteroatom-substituted aldehydes;" Tetrahedron, Elsevier Science Publishers, Amsterdam, NL., vol. 59, No. 6 pp. 767-772 XP004404933 (Feb. 3, 2003).
Database Beilstein [online] Beilstein Institute for Organic Chemistry, Frankfurt-Main, DE; Database accession No. Reaction ID 970178 XP 002571550 (1963).
PCT International Search Report for PCT/EP2009/007139, mailed Mar. 22, 2010.
English translation of the PCT International Preliminary Report on Patentability for PCT/EP2009/007139, mailed Jun. 30, 2011.
PCT International Search Report for PCT/EP2009/007140, mailed Mar. 11, 2010.
English translation of the PCT International Preliminary Report on Patentability for PCT/EP2009/007140, mailed Jun. 30, 2011.
PCT International Search Report for PCT/EP2009/008964, mailed Jul. 9, 2010.
English translation of the PCT International Preliminary Report on Patentability for PCT/EP2009/008964, mailed Jun. 30, 2011.
Alonso et al.: "Transition-Metal Catalyzed Addition of Heteroatom-Hydrogen Bonds to Alkynes;" Chem. Rev., pp. 3148-3153 XP002556525 (2004).
Pudovick et al.: "Free Radical Reaction of Addition of Partial Esters of Phosphorus Acids to Acetylenic Hydrocarbons;" J. Gen. Chem. USSR, vol. 39, No. 5, pp. 986-988 XP009126232 (1969).
Database Beilstein [online] Beilstein Institute for Organic Chemistry, Frankfurt-Main, DE; Database accession No. Reaction BRN 3110535, retrieved from xfire XP002557076 (1967).
Database Beilstein [Online] Beilstein Institute for Organic Chemistry, Frankfurt-Main, DE; Database accession No. Reaction BRN 8075738 XP 002557077 (1997).
PCT International Search Report for PCT/EP2009/007142, mailed Feb. 9, 2010.
English translation of PCT International Preliminary Report on Patentability for PCT/EP2009/007142, mailed Jun. 30, 2011.
English Abstract for SU 314758, Sep. 21, 1971.

(56) References Cited

OTHER PUBLICATIONS

Sasse K Ed—Sasse K: "Houben-Weyl Methoden der Organischen Chemie", Organische Phosphor-Verbindungen; [Methoden der Organischen Chemie], Stuttgart, G. Thieme Verlag DE, XP002500739, pp. 257-259, 261, 294-301 (Jan. 1, 1963).

"1" In: Sasse K Ed — Sasse K: "Houben-Weyl Methoden der Organischen Chemie;" Organische Phosphor-Verbindungen; [Methoden der Organischen Chemie], Stuttgart, G. Thieme Verlag, DE, p. 358, XP002564325 (Jan. 1, 1963).

Regitz:"Houben-Weyl Methoden der Organischen Chemie" Organische Phosphor-Verbindungen;.[Methoden der Organischen Chemie], Stuggart, G. Thieme Verlag, DE, pp. 308-309 XP002564334 (Jan. 1, 1982).

Yamagishi et al.: "Lipase-catalyzed kinetic resolution of alpha-hydroxy-H-phosphinates" Tetrahedron Letters, Elsevier, Amsterdam, NL, vol. 45, No. 36, pp. 6713-6716 XP004556626 (Aug. 30, 2004).

Anderson et al.: "Antidiabetic agents: a new class of reversible carnitine palmitoyltrasferase I inhibitors;" J. Med. Chem., vol. 38, No. 18, pp. 3448-3450 XP002564326 (1995).

Karanewsky et al.: "Synthesis of Phosphinic Monoesters from Phosphonous Acids" Tetrahedron Letters, Elsevier, Amsterdam, NL, vol. 27, No. 16, pp. 1751-1754 XP001084930 (Jan. 1, 1986).

Issleib, et al.: "Synthese und Reaktionsverhalten der Athylen-bis-organophosphine;" Chemische Berichte, vol. 101, pp. 2197-2202 XP009126251 (1968).

PCT International Search Report for PCT/EP2009/007143, mailed Feb. 17, 2010.

English translation of the PCT International Preliminary Report on Patentability for PCT/EP2009/007143, mailed Jun. 30, 2011.

Regitz: "Houben-Weyl Methoden der Organishcen Chemie" p. 188, (Jan. 1, 1982).

Rezenka et al.: "Synthesis of a Bifunctional Monophosphinate DOTA Derivative Having a Free Carboxylate Group in the Phosphorus Side Chain;" Synthesis, Georg Thieme Verlag, Stuttgart pp. 1431-1435 XP009126087 (Sep. 1, 2008).

Database Beilstein [online] Beilstein Institute for Organic Chemistry, Frankfurt-Main, DE; Database accession No. Reaction ID 938840 XP002557780 (1962).

Diel et al.: "Organische Phosphorverbindungen 84. Herstellung Eigenschaften und Biologische Wirkung von Hydrazino-Methyl-Phosphon- und Phosphinsaeuren und Derivatin;" Phosphorus and Sulfur and the Related Elements, Gordon and Breach—Harwood Academic, CH, vol. 36, pp. 85-98 XP001105809 (Jan. 1, 1998).

Sasse K Ed — Sasse K: "Houben-Weyl Methoden der Organischen Chemie", Organische Phosphor-Verbindungen; [Methoden der Organischen Chemie], Stuttgart, G. Thieme Verlag DE, XP002557781, pp. 228-229 (Jan. 1, 1963).

Kielbasinski et al: "Enzymatic reactions in ionic liquids: lipase-catalysed kinetic resolution of racemic, P-chiral hydroxymethanephosphinates and hydroxymethylphosphine oxides;" Tetrahedron Asymmetry, Pergamon Press Ltd, Oxford, GB, vol. 13, No. 7, pp. 735-738 XP004354866 (May 2, 2002).

Maier: "Organic Phosphorus compounds 91.1 Synthesis and Properties of 1-Amino-2-Arylethylphosphinic and—Phosphinic Acids as well as Phosphine Oxides;" Phosphorus, Sulfur and Silicon and the Related Elements, Gordon and Breach Science Publishers, Amsterdam, GB, vol. 53, No. 1/04 pp. 43-67 XP000671624 (Jan. 1, 1990).

US 6,248,921, 06/2001, Weferling et al. (withdrawn)

* cited by examiner

PROCESS FOR PREPARING MONO-ALLYL-FUNCTIONALIZED DIALKYLPHOSPHINIC ACIDS, SALTS AND ESTERS THEREOF WITH ALLYLIC COMPOUNDS, AND THE USE THEREOF

This invention relates to a method for producing monoallyl-functionalized dialkylphosphinic acids, salts and esters by means of allylic compounds and to their use.

Hitherto there are no methods in existence for producing monoallyl-functionalized dialkylphosphinic acids, esters and salts that are available economically and on a large industrial scale and more particularly enable a high space-time yield to be achieved. Nor are there any methods that are sufficiently effective without unwelcome halogen compounds as starting materials, nor any where the end products are easy to obtain or isolate or else obtainable in a specific and desirable manner under controlled reaction conditions (such as a transesterification for example).

We have found that this object is achieved by a method for producing monoallyl-functionalized dialkylphosphinic acids, esters and salts, which comprises a) reacting a phosphinic acid source (I)

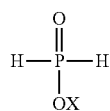
(I)

with olefins (IV)

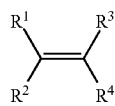
(IV)

in the presence of a catalyst A to form an alkylphosphonous acid, salt or ester

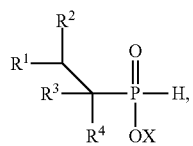
(II)

b) reacting the resulting alkylphosphonous acid, salt or ester (II) with allylic compounds of the formula (V)

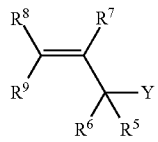
(V)

in the presence of a catalyst B and a base to form a monoallyl-functionalized dialkylphosphinic acid derivative (III)

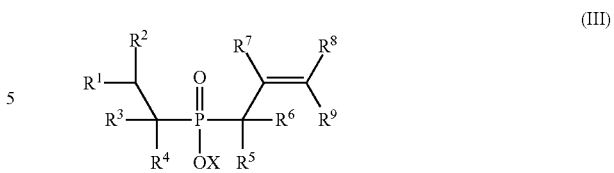
(III)

where $R^1$, $R^2$, $R^3$, $R^4$, $R^5$, $R^6$, $R^7$, $R^8$, $R^9$ are identical or different and are each independently H, $C_1$-$C_{18}$-alkyl, $C_6$-$C_{18}$-aryl, $C_6$-$C_{18}$-aralkyl, $C_6$-$C_{18}$-alkylaryl, CN, CHO, $OC(O)CH_2CN$, $CH(OH)C_2H_5$, $CH_2CH(OH)CH_3$, 9-anthracene, 2-pyrrolidone, $(CH_2)_mOH$, $(CH_2)_mNH_2$, $(CH_2)_mNCS$, $(CH_2)_mNC(S)NH_2$, $(CH_2)_mSH$, $(CH_2)_mS$-2-thiazoline, $(CH_2)_mSiMe_3$, $C(O)R^{10}$, $(CH_2)_mC(O)R^{10}$, $CH=CHR^{10}$ and/or $CH=CH-C(O)R^{10}$ and where $R^{10}$ is $C_1$-$C_8$-alkyl or $C_6$-$C_{18}$-aryl and m is an integer from 0 to 10 and X is H, $C_1$-$C_{18}$-alkyl, $C_6$-$C_{18}$-aryl, $C_6$-$C_{18}$-aralkyl, $C_6$-$C_{18}$-alkylaryl, $(CH_2)_kOH$, $CH_2$—$CHOH$—$CH_2OH$, $(CH_2)_kO(CH_2)_kH$, $(CH_2)_k$—$CH(OH)$—$(CH_2)_kH$, $(CH_2$—$CH_2O)_kH$, $(CH_2$—$C[CH_3]HO)_kH$, $(CH_2$—$C[CH_3]HO)_k(CH_2$—$CH_2O)_kH$, $(CH_2$—$CH_2O)_k(CH_2$—$C[CH_3]HO)H$, $(CH_2$—$CH_2O)_k$-alkyl, $(CH_2$—$C[CH_3]HO)_k$-alkyl, $(CH_2$—$C[CH_3]HO)_k(CH_2$—$CH_2O)_k$-alkyl, $(CH_2$—$CH_2O)_k(CH_2$—$C[CH_3]HO)$ O-alkyl, $(CH_2)_k$—$CH=CH(CH_2)_kH$, $(CH_2)_kNH_2$ and/or $(CH_2)_kN[(CH_2)_kH]_2$, where k is an integer from 0 to 100, and/or Mg, Ca, Al, Sb, Sn, Ge, Ti, Fe, Zr, Zn, Ce, Bi, Sr, Mn, Cu, Ni, Li, Na, K, H and/or a protonated nitrogen base and Y is a halogen or acetate and the catalysts A and B comprise transition metals and/or transition metal compounds and/or catalyst systems composed of a transition metal and/or transition metal compound and at least one ligand.

Preferably, the monoallyl-functionalized dialkylphosphinic acid, its salt or ester (III) obtained after step b) is subsequently reacted in a step c) with metal compounds of Mg, Ca, Al, Sb, Sn, Ge, Ti, Fe, Zr, Zn, Ce, Bi, Sr, Mn, Li, Na, K and/or a protonated nitrogen base to form the corresponding monoallyl-functionalized dialkylphosphinic acid salts (III) of these metals and/or of a nitrogen compound.

Preferably, the alkylphosphonous acid, salt or ester (II) obtained after step a) and/or the monoallyl-functionalized dialkylphosphinic acid, salt or ester (III) obtained after step b) and/or the particular resulting reaction solution thereof are esterified with an alkylene oxide or an alcohol M-OH and/or M'-OH, and the respectively resulting alkylphosphonous ester (II) and/or monoallyl-functionalized dialkylphosphinic ester (III) are subjected to the further reaction steps b) or c).

Preferably, the groups $C_6$-$C_{18}$-aryl, $C_6$-$C_{18}$-aralkyl and $C_6$-$C_{18}$-alkylaryl are substituted with $SO_3X_2$, —$C(O)CH_3$, OH, $CH_2OH$, $CH_3SO_3X_2$, $PO_3X_2$, $NH_2$, $NO_2$, $OCH_3$, SH and/or $OC(O)CH_3$.

Preferably, $R^1$, $R^2$, $R^3$, $R^4$, $R^5$, $R^6$, $R^7$, $R^8$, $R^9$ are identical or different and are each independently H, methyl, ethyl, n-propyl, isopropyl, n-butyl, isobutyl, tert-butyl and/or phenyl.

Preferably, X is Ca, Al, Zn, Ti, Mg, Ce, Fe, methyl, ethyl, n-propyl, isopropyl, n-butyl, isobutyl, tert-butyl, phenyl, ethylene glycol, propyl glycol, butyl glycol, pentyl glycol, hexyl glycol, allyl and/or glycerol.

Preferably m=1 to 10 and k=2 to 10.

Preferably, the catalyst systems A and B are each formed by reaction of a transition metal and/or of a transition metal compound and at least one ligand.

Preferably, the transition metals and/or transition metal compounds comprise such from the seventh and eighth transition groups.

Preferably, the transition metals and/or transition metal compounds comprise rhodium, ruthenium, nickel, palladium, platinum.

Preferably, the allylic compounds (V) comprise 3-chloro-1-propene, 3-chloro-2-methyl-1-propene, 3-chloro-1-phenyl-1-propene, 1-chloro-2-butene, 1-chloro-3-methyl-2-butene, 3-bromo-1-propene, 3-bromo-2-methyl-1-propene, 3-bromo-1-phenyl-1-propene, 1-bromo-2-butene, 1-bromo-3-methyl-2-butene, allyl acetate, 2-methylallyl acetate.

Preferably, the base comprises alkali and/or alkaline earth metals, alkali metal hydrides and/or alkoxides and/or hydroxides, alkaline earth metal hydrides and/or alkoxides and/or hydroxides, amines and/or diamines or organolithium compounds.

Preferably, the alcohol of the general formula M-OH comprises linear or branched, saturated and unsaturated, monohydric organic alcohols having a carbon chain length of $C_1$-$C_{18}$ and the alcohol of the general formula M'-OH comprises linear or branched, saturated and unsaturated polyhydric organic alcohols having a carbon chain length of $C_1$-$C_{18}$.

The present invention additionally provides for the use of monoallyl-functionalized dialkylphosphinic acids, salts and esters obtained according to one or more of claims 1 to 11 as an intermediate for further syntheses, as a binder, as a crosslinker or accelerant to cure epoxy resins, polyurethanes and unsaturated polyester resins, as polymer stabilizers, as crop protection agents, as a therapeutic or additive in therapeutics for humans and animals, as a sequestrant, as a mineral oil additive, as a corrosion control agent, in washing and cleaning applications and in electronic applications.

The present invention likewise provides for the use of monoallyl-functionalized dialkylphosphinic acids, salts and esters (III) obtained according to one or more of claims 1 to 11 as a flame retardant, more particularly as a flame retardant for clearcoats and intumescent coatings, as a flame retardant for wood and other cellulosic products, as a reactive and/or non-reactive flame retardant for polymers, in the manufacture of flame-retardant polymeric molding materials, in the manufacture of flame-retardant polymeric molded articles and/or for flame-retardant finishing of polyester and cellulose straight and blend fabrics by impregnation.

The present invention also provides a flame-retardant thermoplastic or thermoset polymeric molding material containing 0.5% to 45% by weight of monoallyl-functionalized dialkylphosphinic acids, salts or esters (III) obtained according to one or more of claims 1 to 11, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

Lastly, the invention also provides flame-retardant thermoplastic or thermoset polymeric molded articles, films, threads and fibers containing 0.5% to 45% by weight of monoallyl-functionalized dialkylphosphinic acids, salts or esters (III) obtained according to one or more of claims 1 to 11, 0.5% to 95% by weight of thermoplastic or thermoset polymer or mixtures thereof, 0% to 55% by weight of additives and 0% to 55% by weight of filler or reinforcing materials, wherein the sum total of the components is 100% by weight.

All the aforementioned reactions can also be carried out in stages; similarly, the various processing steps can also utilize the respective resulting reaction solutions.

When the monoallyl-functionalized dialkylphosphinic acid (III) after step b) comprises an ester, an acidic or basic hydrolysis may preferably be carried out in order that the free monoallyl-functionalized dialkylphosphinic acid or salt may be obtained.

Preferably, the target compounds to be produced, i.e., the monoallyl-functionalized dialkylphosphinic acids, comprise ethylpropenylphosphinic acid, propylpropenyl-phosphinic acid, i-propylpropenylphosphinic acid, butylpropenylphosphinic acid, sec-butylpropenylphosphinic acid, i-butylpropenylphosphinic acid, 2-phenylethyl-propenylphosphinic acid, ethyl(2-methylpropenyl)phosphinic acid, propyl(2-methylpropenyl)phosphinic acid, i-propyl(2-methylpropenyl)phosphinic acid, butyl(2-methylpropenyl)phosphinic acid, sec-butyl(2-methylpropenyl)phosphinic acid, i-butyl(2-methylpropenyl)phosphinic acid, 2-phenylethyl(2-methylpropenyl)-phosphinic acid, ethyl(2-butenyl)phosphinic acid, propyl(2-butenyl)phosphinic acid, i-propyl(2-butenyl)phosphinic acid, butyl(2-butenyl)phosphinic acid, sec-butyl(2-butenyl)phosphinic acid, i-butyl(2-butenyl)phosphinic acid, 2-phenylethyl-(2-butenyl)phosphinic acid, ethyl(3-methyl-2-butenyl)phosphinic acid, propyl(3-methyl-2-butenyl)phosphinic acid, i-propyl(3-methyl-2-butenyl)phosphinic acid, butyl(3-methyl-2-butenyl)phosphinic acid, sec-butyl(3-methyl-2-butenyl)phosphinic acid, i-butyl(3-methyl-2-butenyl)phosphinic acid, 2-phenylethyl(3-methyl-2-butenyl)phosphinic acid, the esters comprise methyl, ethyl, i-propyl, butyl, phenyl, 2-hydroxyethyl, 2-hydroxypropyl, 3-hydroxypropyl, 4-hydroxybutyl and/or 2,3-dihydroxypropyl esters of the aforementioned monoallyl-functionalized dialkylphosphinic acids, and the salts comprise an aluminum (III), calcium(II), magnesium(II), cerium(III), titanium(IV) and/or zinc(II) salt of the aforementioned monoallyl-functionalized dialkylphosphinic acids.

Preferably, the transition metals for catalyst A comprise elements of the seventh and eighth transition groups (a metal of group 7, 8, 9 or 10, in modern nomenclature), for example rhenium, ruthenium, cobalt, rhodium, iridium, nickel, palladium and platinum.

Preference for use as source of the transition metals and transition metal compounds is given to their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for example trifluoroacetate, trichloroacetate.

A further source of the transition metals and transition metal compounds is salts of the transition metals with tetraphenylborate and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preference for use as a source of the transition metals is given to the transition metal as an element and/or a transition metal compound in its zerovalent state.

Preferably, the transition metal salt is used as a metal, or as an alloy with further metals, in which case boron, zirconium, tantalum, tungsten, rhenium, cobalt, iridium, nickel, palladium, platinum and/or gold is preferred here. The transition metal content in the alloy used is preferably 45-99.95% by weight.

Preferably, the transition metal is used in microdisperse form (particle size 0.1 mm-100 μm).

Preferably, the transition metal is used supported on a metal oxide such as, for example, alumina, silica, titanium dioxide, zirconium dioxide, zinc oxide, nickel oxide, vandium oxide, chromium oxide, magnesium oxide, Celite®, diatomaceous earth, on a metal carbonate such as, for example, barium carbonate, calcium carbonate, strontium carbonate, on a metal sulfate such as, for example, barium sulfate, calcium sulfate, strontium sulfate, on a metal phosphate such as, for example, aluminum phosphate, vanadium phosphate, on a metal carbide such as, for example, silicone carbide, on a metal aluminate such as, for example, calcium aluminate, on a metal silicate such as, for example, aluminum silicate, chalks, zeolites, bentonite, montmorillonite, hectorite, on functionalized silicates, functionalized silica gels such as, for example, SiliaBond®, QuadraSil™, on functionalized polysiloxanes such as, for example, Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers such as, for example, Amberlite™, Amberjet™, Ambersep™, Dowex®, Lewatit®, ScavNet®, on functionalized polymers such as, for example, Chelex®, QuadraPure™, Smopex®, PolyOrgs®, on polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example
palladium, platinum, nickel, rhodium; palladium platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanide-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium (II) hydride, palladium(II) oxide, palladium(II) peroxide, palladium(II) cyanide, palladium(II) sulfate, palladium(II) nitrate, palladium(II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;
nickel(II) chloride, nickel(II) bromide, nickel(II) iodide, nickel(II) fluoride, nickel(II) hydride, nickel(II) oxide, nickel (II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel (II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel (II) thiocyanate, nickel(II) bis(2,2,6,6-tetramethyl-3,5-heptanedionate), nickel(II) propionate, nickel(II) acetate, nickel (II) stearate, nickel(II) 2-ethylhexanoate, nickel(II) acetylacetonate, nickel(II) hexafluoroacetylacetonate, nickel (II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

platinum(II) chloride, platinum(II) bromide, platinum(II) iodide, platinum(II) fluoride, platinum(II) hydride, platinum(II) oxide, platinum(II) peroxide, platinum(II) cyanide, platinium(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinium(II) stearate, platinium(II) 2-ethylhexanoate, platinium(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclopentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(II) 2,9,16,23-tetraphenoxy-29H,31H-phthalocyanine, platinum(II) 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenyl-sulfinyl)ethane, 1,3-bis(2,6-diisopropylphenyl)imidazolidene)(3-chloropyridyl), 2'-(dimethylamino)-2-biphenylyl, dinorbornyiphosphine, 2-(dimethylamino-methyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethyl hexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)imidazol-2-ylidene, 1,3-bis(mesityl)imidazol-2-ylidene, 1,1'-bis(diphenylphosphino)ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I) dimer, (2-methylallyl)palladium (II) chloride dimer, bis(dibenzylideneacetone)palladium(0), tris(dibenzylideneacetone)dipalladium(0), tetrakis(triphenylphosphine)palladium(0), tetrakis(tricyclohexylphosphine)-palladium(0), bis[1,2-bis(diphenylphosphine)ethane] palladium(0), bis(3,5,3',5'-dimethoxydibenzylideneacetone) palladium(0), bis(tri-tert-butylphosphine)palladium(0), meso-tetraphenyltetrabenzoporphinepalladium, tetrakis(methyldiphenylphosphine)palladium(0), tris(3,3',3"-phosphinidyne-tris(benzenesulfonato)palladium(0) nonasodium salt, 1,3-bis(2,4,6-trimethylphenyl)imidazol-2-ylidene(1,4-naphthoquinone)palladium(0), 3-bis(2,6-diisopropylphenyl)imidazol-2-ylidene(1,4-naphthoquinone)palladium(0) and the chloroform complex thereof;
allylnickel(II) chloride dimer, ammoniumnickel(II) sulfate, bis(1,5-cycloocta-diene)nickel(0), bis(triphenylphosphine) dicarbonylnickel(0), tetrakis(triphenyl-phosphine)nickel(0), tetrakis(triphenyl phosphite)nickel(0), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate (IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diammintetrachloroplatinum (IV), potassium trichloro(ethylene)platinate(II), sodium hexahydroxyplatinate(IV) tetraamineplatinum(II) tetrachloroplatinate(II), tetrabutylammonium hexachloroplatinate (IV), ethylenebis(triphenylphosphine)platinum(0), platinum (0) 1,3-divinyl-1,1,3,3-tetramethyldisiloxane, platinum(0) 2,4,6,8-tetramethyl-2,4,6,8-tetravinylcyclotetrasiloxane, tetrakis(triphenylphosphine)platinum(0), platinum octaethylporphyrine, chloroplatinic acid, carboplatin; chlorobis(ethylene)rhodium dimer, hexarhodium hexadecacarbonyl, chloro(1,5-cyclooctadiene)rhodium dimer, chloro(norbornadiene)rhodium dimer, chloro(1,5-hexadiene)rhodium dimer.

The ligands preferably comprise phosphines of the formula (VI)

where the $R^{11}$ radicals are each independently hydrogen, straight-chain, branched or cyclic $C_1$-$C_{20}$-alkyl, $C_1$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives and/or phenyl substituted by at least one $R^{12}$, or naphthyl substituted by at least one $R^{12}$. $R^{12}$ in each occurrence is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —$OCO(C_1$-$C_{20}$-alkyl), $NHCO(C_1$-$C_{20}$-alkyl), —$SO_3M$, —$SO_2N(R^{13})M$, —$CO_2M$, —$PO_3M_2$, —$AsO_3M_2$, —$SiO_2M$, —$C(CF_3)_2OM$ (M=H, Li, Na or K), where $R^{13}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_1$-$C_{20}$-alkenyloxy, $C_1$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_1$-$C_{20}$-arylalkyl, $C_1$-$C_{20}$-alkylaryl, phenyl and/or biphenyl. Preferably, the $R^{11}$ groups are all identical.

Suitable phosphines(VI) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctylphosphine, tridecylphosphine, triphenylphosphine, diphenylmethylphosphine, phenyldimethylphosphine, tri(o-tolyl)phosphine, tri(p-tolyl) phosphine, ethyldiphenylphosphine, dicyclohexylphenylphosphine, 2-pyridyl-diphenylphosphine, bis(6-methyl-2-pyridyl)phenylphosphine, tri(p-chlorophenyl)-phosphine, tri(p-methoxyphenyl)phosphine, diphenyl(2-sulfonatophenyl)-phosphine; potassium, sodium and ammonium salts of diphenyl(3-sulfonatophenyl)phosphine, bis(4,6-dimethyl-3-sulfonatophenyl)(2,4-dimethylphenyl)phosphine, bis(3-sulfonatophenyl)phenylphosphines, tris(4,6-dimethyl-3-sulfonatophenyl)phosphines, tris (2-sulfonatophenyl)phosphines, tris(3-sulfonatophenyl) phosphines; 2-bis(diphenylphosphinoethyl) trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the general formula

In this formula, each M" independently is N, P, As or Sb.

M" is preferably the same in the two occurrences and more preferably is a phosphorus atom.

Each $R^{11}$ group independently represents the radicals described under formula (VI). The $R^{11}$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—O—$CH_2$—, —$CH_2$—$CH_2$—$CH_2$—$CH_2$—, —$CH_2$—$CH(C_2H_5)$—$CH_2$—, —$CH_2$—$CH(n\text{-}Pr)$—$CH$— and —$CH_2$—$CH(n\text{-}Bu)$—$CH_2$—, substituted or unsubstituted 1,2-phenyl, 1,2-cyclohexyl, 1,1'- or 1,2-ferrocenyl radicals, 2,2'-(1,1'-biphenyl), 4,5-xanthene and/or oxydi-2,1-phenylene radicals.

Examples of suitable bidentate phosphine ligands (VII) are for example 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-tert-butylphosphino)ethane, bis(dicyclohexylphosphino)ethane, 1,2-bis(diphenylphosphino) ethane; 1,3-bis(dicyclohexylphosphino)propane, 1,3-bis (diisopropylphosphino)propane, 1,3-bis(di-tert-butylphosphino)propane, 1,3-bis(diphenylphosphino) propane; 1,4-bis(diisopropylphosphino)butane, 1,4-bis (diphenylphosphino)butane; 1,5-bis (dicyclohexylphosphino)pentane; 1,2-bis(di-tert-butylphosphino)benzene, 1,2-bis(diphenylphosphino) benzene, 1,2-bis(dicyclohexylphosphino)benzene, 1,2-bis (dicyclopentylphosphino)benzene, 1,3-bis(di-tert-butylphosphino)benzene, 1,3-bis(diphenylphosphino) benzene, 1,3-bis(dicyclohexylphosphino)benzene, 1,3-bis (dicyclopentylphosphino)benzene; 9,9-dimethyl-4,5-bis (diphenylphosphino)-xanthene, 9,9-dimethyl-4,5-bis (diphenylphosphino)-2,7-di-tert-butylxanthene, 9,9-dimethyl-4,5-bis(di-tert-butylphosphino)xanthene, 1,1'-bis(diphenylphosphino)-ferrocene, 2,2'-bis(diphenylphosphino)-1,1'-binaphthyl, 2,2'-bis(di-p-tolylphosphino)-1,1'-binaphthyl, (oxydi-2,1-phenylene)bis(diphenylphosphine), 2,5-(diisopropylphospholano)benzene, 2,3-O-isopropylidene-2,3-dihydroxy-1,4-bis(diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphosphino)-2'-(N,N-dimethylamino)biphenyl, 2-(diphenylphosphino)ethylamine, 2-[2-(diphenylphosphino)ethyl]pyridine; potassium, sodium and ammonium salts of 1,2-bis(di-4-sulfonatophenylphosphino)benzene, (2,2'-bis[[bis(3-sulfonatophenyl)phosphino]methyl]-4,4',7,7'-tetrasulfonato-1,1'-binapthyl, (2,2'-bis[[bis(3-sulfonatophenyl)phosphino]methyl]-5,5'-tetrasulfonato-1,1'-biphenyl, (2,2'-bis[[bis(3-sulfonatophenyl)phosphino]methyl]-1,1'-binapthyl, (2,2'-bis[[bis(3-sulfonatophenyl)phosphino]methyl]-1,1'-biphenyl, 9,9-dimethyl-4,5-bis(diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)benzene, meso-tetrakis(4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl)porphine and 5,11,17,23-sulfonato-25,26,27,28-tetrahydroxycalix[4]arene.

Moreover, the ligands of the formula (VI) and (VII) can be attached to a suitable polymer or inorganic substrate by the $R^{11}$ radicals and/or the bridging group.

The molar transition metal/ligand ratio of the catalyst system is in the range 1:0.01 to 1:100, preferably in the range from 1:0.05 to 1:10 and more preferably in the range from 1:1 to 1:4.

The reactions in the process stages a), b) and c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the components and/or the transition metal and/or the transition metal compound and/or catalyst system and/or the ligand and/or starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

It is preferable for an intensive commixing of the respective reactants etc. to be effected by an energy input in the range from 0.080 to 10 kW/m³, preferably 0.30-1.65 kW/m³.

During the reaction, the particular catalyst A or B is preferably homogeneous and/or heterogeneous in action. Therefore, the particular heterogeneous catalyst is effective during the reaction as a suspension or bound to a solid phase.

Preferably, the particular catalyst A or B is generated in situ before the reaction and/or at the start of the reaction and/or during the reaction.

Preferably, the particular reaction takes place in a solvent as a single-phase system in homogeneous or heterogeneous mixture and/or in the gas phase.

When a multi-phase system is used, a phase transfer catalyst may be used in addition.

The reactions of the present invention can be carried out in liquid phase, in the gas phase or else in supercritical phase. The particular catalyst A or B is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc. One or more of these compounds can be used, alone or in combination.

Suitable solvents also encompass the phosphinic acid sources and olefins used. These have advantages in the form of higher space-time yield.

It is preferable that the reaction be carried out under the autogenous vapor pressure of the olefin and/or of the solvent.

Preferably, $R^1$, $R^2$, $R^3$ and $R^4$ of olefin (IV) are the same or different and each is independently H, methyl, ethyl, n-propyl, isopropyl, n-butyl, isobutyl, tert-butyl and/or phenyl.

Preference is also given to using functionalized olefins such as allyl isothiocyanate, allyl methacrylate, 2-allylphenol, N-allylthiourea, 2-(allylthio)-2-thiazoline, allyltrimethylsillane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2- hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and 1-vinyl-2-pyrrolidone.

The partial pressure of the olefin during the reaction is preferably 0.01-100 bar and more preferably 0.1-10 bar.

The phosphinic acid/olefin molar ratio for the reaction is preferably in the range from 1:10 000 to 1:0.001 and more preferably in the range from 1:30 to 1:0.01.

The phosphinic acid/catalyst molar ratio for the reaction is preferably in the range from 1:1 to 1:0.00000001 and more preferably a phosphinic acid/catalyst molar ratio in the range from 1:0.01 to 1:0.000001.

The phosphinic acid/solvent molar ratio for the reaction is preferably in the range from 1:10 000 to 1:0 and more preferably a phosphinic acid/solvent molar ratio in the range from 1:50 to 1:1.

One method the present invention provides for producing compounds of the formula (II) comprises reacting a phosphinic acid source with olefins in the presence of a catalyst and freeing the product (II) (alkylphosphonous acid, salts or esters) of catalyst, transition metal or transition metal compound as the case may be, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 of the present invention and/or distillation with auxiliary 2 of the present invention.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, Poly-Orgs®; polymer-bound phosphanes, phosphane oxides, phosphinates, phosphonates, phosphates, amines, ammonium salts, amides, thioamides, urea, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

It is preferable that the amounts added of auxiliary 1 correspond to 0.1-40% by weight loading of the metal on auxiliary 1.

It is preferable that auxiliary 1 be used at temperatures of from 20 to 90° C.

It is preferable that the residence time of auxiliary 1 be from 0.5 to 360 minutes.

Auxiliary 2 is preferably the aforementioned solvent of the present invention.

The esterification of the monoallyl-functionalized dialkylphosphinic acid (III) or of the alkylphosphonous acid derivatives (II) and also of the phosphinic acid source (I) to form the corresponding esters can be achieved for example by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the general formula M-OH and/or M'-OH or by reaction with alkylene oxides, as indicated hereinbelow.

M-OH preferably comprises primary, secondary or tertiary alcohols having a carbon chain length of $C_1$-$C_{18}$. Particular preference is given to methanol, ethanol, propanol, isopropanol, n-butanol, 2-butanol, tert-butanol, amyl alcohol and/or hexanol.

M'-OH preferably comprises ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Also useful as M-OH and M'-OH are mono- or polyhydric unsaturated alcohols having a carbon chain length of $C_1$-$C_{18}$, for example n-but-2-en-1-ol, 1,4-butenediol and allyl alcohol.

Also useful as M-OH and M'-OH are reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethylhexyloxy)ethanol, 2-n-dodecoxyethanol, methyl diglycol, ethyl diglycol, isopropyl diglycol, fatty alcohol polyglycol ethers and aryl polyglycol ethers.

M-OH and M'-OH are also preferably reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Useful M-OH and M'-OH further include reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preference for use as M-OH and M'-OH is also given to reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Also useful as M-OH and M'-OH are reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanolamine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxybutane, 1,2-epoxyethylbenzene, (2,3-epoxypropyl)benzene, 2,3-epoxy-1-propanol and 3,4-epoxy-1-butene.

Suitable solvents are the solvents mentioned in the process step a) and also the M-OH and M'-OH alcohols used and the alkylene oxides. These offer advantages in the form of a higher space-time yield.

The reaction is preferably carried out under the autogenous vapor pressure of the employed alcohol M-OH, M'-OH and alkylene oxide and/or of the solvent.

Preferably, the reaction is carried out at a partial pressure of the employed alcohol M-OH, M'-OH and alkylene oxide of 0.01-100 bar, more preferably at a partial pressure of the alcohol of 0.1-10 bar.

The reaction is preferably carried out at a temperature in the range from −20 to 340° C. and is more preferably carried out at a temperature in the range from 20 to 180° C.

The reaction is preferably carried out at a total pressure in the range from 1 to 100 bar.

The reaction is preferably carried out in a molar ratio for the alcohol or alkylene oxide component to the phosphinic acid source (I) or alkylphosphonous acid (II) or monoallyl-functionalized dialkylphosphinic acid (III) ranging from 10 000:1 to 0.001:1 and more preferably from 1000:1 to 0.01:1.

The reaction is preferably carried out in a molar ratio for the phosphinic acid source (I) or alkylphosphonous acid (II) or monoallyl-functionalized dialkylphosphinic acid (III) to the solvent ranging from 1:10 000 to 1:0 and more preferably in a phosphinic acid/solvent molar ratio ranging from 1:50 to 1:1.

The catalyst B as used for process step b) for the reaction of the alkylphosphonous acid, salts or esters (II) with an allylic compound (V) and a base to form the monoallyl-functionalized dialkylphosphinic acid, salts and esters (III) may preferably be the catalyst A.

Preferably, the base comprises alkali and/or alkaline earth metals, alkali metal hydrides and/or alkoxides and/or hydroxides, alkaline earth metal hydrides and/or alkoxides and/or hydroxides, amines and/or diamines and/or organolithium compounds.

Preferred alkali and/or alkaline earth metal compounds are lithium, lithium hydroxide, lithium hydride, lithium aluminohydride, methyllithium, butyllithium, t-butyllithium, lithium diisopropylamide, sodium, sodium hydroxide, sodium hydride, sodium borohydride, sodium methoxide, sodium ethoxide, sodium butoxide, potassium hydroxide, potassium methoxide, potassium ethoxide and/or potassium butoxde.

Preferred amines are ammonia, monoamines, diamines.

Preferred monoamines are for example amines of the formula R'—NH$_2$, where R' represents linear or branched C$_1$-C$_{20}$-alkyl. Preference is given to methylamine, ethylamine, propylamines, i-propylamine, butylamine, i-butylamine, pentylamine and 2-ethylhexylamine, aniline.

Preferred diamines are for example amines of the formula H$_2$N—R"—NH$_2$, where R" represents linear or branched C$_1$-C$_{20}$-alkyl. Preference is given to ethylene-diamine, propylenediamine, diaminobutane, pentamethylenediamine and hexamethylenediamine.

Preferred bases further include the compounds known as proton sponges such as, for example, 1,8-diazabicyclo[5.4.0]undec-7-ene, 1,5,7-triazabicyclo[4.4.0]dec-5-ene, 1,1,3,3-tetramethylguanidine.

Preference for use as allylic compounds is given to 3-chloro-1-propene, 3-chloro-2-methyl-1-propene, 3-chloro-1-phenyl-1-propene, 1-chloro-2-butene, 1-chloro-3-methyl-2-butene, 3-bromo-1-propene, 3-bromo-2-methyl-1-propene, 3-bromo-1-phenyl-1-propene, 1-bromo-2-butene, 1-bromo-3-methyl-2-butene, allyl acetate, 2-methylallyl acetate.

Preferably, the proportion of base based on the allylic compound (V) used is in the range from 0.01 to 110 mol %.

The reaction is preferably carried out at temperatures of 20 to 120° C. and more preferably at 30 to 80° C.

The reaction time is preferably in the range from 0.1 to 20 hours.

The reaction is preferably carried out under the autogenous vapor pressure of the allylic compound (V) and/or of the solvent.

Suitable solvents for process stage b) are those used above in process stage a).

The reaction is preferably carried out at a partial pressure of the allylic compound (V) from 0.01-100 bar, more preferably at 0.1-10 bar.

The ratio of allylic compound (V) to alkylphosphonous acid (II) is preferably in the range from 2:1 to 1:1 and more preferably in the range from 1.1:1 to 1:1.

The reaction is preferably carried out in an alkylphosphonous acid/catalyst molar ratio of 1:1 to 1:0.00000001 and more preferably in an alkylphosphonous acid/catalyst molar ratio of 1:0.25 to 1:0.000001.

The reaction is preferably carried out in an alkylphosphonous acid/solvent molar ratio of 1:10 000 to 1:0 and more preferably in an alkylphosphonous acid/solvent molar ratio of 1:50 to 1:1.

The monoallyl-functionalized dialkylphosphinic acid or salt (III) can thereafter be converted into further metal salts.

The metal compounds which are used in process stage c) preferably comprise compounds of the metals Mg, Ca, Al, Sb, Sn, Ge, Ti, Fe, Zr, Zn, Ce, Bi, Sr, Mn, Li, Na, K, more preferably Mg, Ca, Al, Ti, Zn, Sn, Ce, Fe.

Suitable solvents for process stage c) are those used above in process stage a).

The reaction of process stage c) is preferably carried out in an aqueous medium.

Process stage c) preferably comprises reacting the monoallyl-functionalized dialkylphosphinic acids, esters and/or alkali metal salts (III) obtained after process stage b) with metal compounds of Mg, Ca, Al, Zn, Ti, Sn, Zr, Ce or Fe to form the monoallyl-functionalized dialkylphosphinic acid salts (III) of these metals.

The reaction is carried out in a molar ratio of monoallyl-functionalized dialkylphosphinic acid, ester or salt (III) to metal in the range from 8:1 to 1:3 (for tetravalent metal ions or metals having a stable tetravalent oxidation state), from 6:1 to 1:3 (for trivalent metal ions or metals having a stable trivalent oxidation state), from 4:1 to 1:3 (for divalent metal ions or metals having a stable divalent oxidation state) and from 3:1 to 1:4 (for monovalent metal ions or metals having a stable monovalent oxidation state).

Preferably, monoallyl-functionalized dialkylphosphinic acid, ester or salt (III) obtained in process stage b) is converted into the dialkylphosphinic acid and the latter is reacted in process stage c) with metal compounds of Mg, Ca, Al, Zn, Ti, Sn, Zr, Ce or Fe to form the monoallyl-functionalized dialkylphosphinic acid salts (III) of these metals.

Preferably, monoallyl-functionalized dialkylphosphinic acid/ester obtained in process stage b) is converted to a dialkylphosphinic acid alkali metal salt and the latter is reacted in process stage c) with metal compounds of Mg, Ca, Al, Zn, Ti, Sn, Zr, Ce or Fe to form the monoallyl-functionalized dialkylphosphinic acid salts (III) of these metals.

The metal compounds of Mg, Ca, Al, Zn, Ti, Sn, Zr, Ce or Fe for process stage c) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate, thiocyanate oxide, oxide hydroxide, their corresponding hydrates and/or polyaluminum hydroxy compounds, which preferably have an aluminum content of 9 to 40% by weight.

Also suitable are aluminum salts of mono-, di-, oligo-, polycarboxylic acids such as, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts such as for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxoacids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxoacids of transition metals (for example zinc chromate(VI) hydroxide, chromite, molybdate, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

In the case of titanium compounds, metallic titanium is as is titanium(III) and/or (IV) chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred as are zirconium salts such as zirconium chloride, zirconium sulfate, zirconyl acetate, zirconyl chloride. Zirconium oxides and also zirconium (IV) tert-butoxide are also preferred.

The reaction is preferably carried out at a solids content of the monoallyl-functionalized dialkylphosphinic acid salts (III) in the range from 0.1% to 70% by weight, preferably 5% to 40% by weight.

The reaction in process stage c) is preferably carried out at a temperature of 20 to 250° C. and more preferably at a temperature of 80 to 120° C.

The reaction in process stage d) is preferably carried out at a pressure between 0.01 and 1000 bar and more preferably 0.1 to 100 bar.

The reaction in process stage d) preferably takes place during a reaction time in the range from $1*10^{-7}$ to $1*10^2$ h.

Preferably, the monoallyl-functionalized dialkylphosphinic acid salt (III) removed after process stage d) from the reaction mixture by filtration and/or centrifugation is dried.

Preferably, the product mixture obtained after process stage b) is reacted with the metal compounds without further purification.

Preferred solvents are the solvents mentioned in process step a).

The reaction in process stage b) and/or c) is preferably carried out in the solvent system given by stage a) and/or b).

The reaction in process stage c) is preferred in a modified given solvent system. The solvent is preferably modified by adding acidic components, solubilizers, foam inhibitors, etc.

In a further embodiment of the method, the product mixture obtained after process stage a) and/or b) is worked up.

In a further embodiment of the method, the product mixture obtained after process stage b) is worked up and thereafter the monoallyl-functionalized dialkylphosphinic acids and/or salts or esters (III) obtained after process stage b) are reacted in process stage c) with the metal compounds.

Preferably, the product mixture after process stage b) is worked up by isolating the monoallyl-functionalized dialkylphosphinic acids and/or salts or esters (III). In this case, the isolating step is carried out by removing the solvent system, for example by evaporation.

Preferably, the monoallyl-functionalized dialkylphosphinic acid salt (III) of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 μm, preferably of 10 to 500 μm, a bulk density of 80 to 800 g/l, preferably 200 to 700 g/l, and a Pfrengle flowability of 0.5 to 10, preferably of 1 to 5.

The molded articles, films, threads and fibers more preferably contain from 5% to 30% by weight of the monoallyl-functionalized dialkylphosphinic acid/ester/salts produced according to one or more of claims 1 to 12, from 5% to 90% by weight of polymer or mixtures thereof, from 5% to 40% by weight of additives and from 5% to 40% by weight of filler, wherein the sum total of the components is always 100% by weight.

Preference is given to a flame retardant containing 0.1 to 90% by weight of the monoallyl-functionalized dialkylphosphinic acid, ester and salts (III) and 0.1% to 50% by weight of further additives.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, nucleus-forming agents, nucleating agents, additives for laser marking, hydrolysis stabilizers, chain extenders, color pigments, softeners, plasticizers and/or plasticizing agents.

More particularly, the present invention provides for the use of the present invention monoallyl-functionalized dialkylphosphinic acid, esters and salts (III) as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters are derived from dicarboxylic acids and their esters and diols and/or from hydroxycarboxylic acids or the corresponding lactones.

It is particularly preferable to use terephthalic acid and ethylene glycol, 1,3-propanediol and 1,3-butanediol.

Polymer production may preferably proceed by adding customary additives (crosslinking agents, matting agents and stabilizing agents, nucleating agents, dyes and fillers, etc) in addition to the customary catalysts.

The flame-retardant polymer molding materials produced according to the present invention are preferably used in polymer molded articles.

Preferred polymer molded articles are threads, fibers, self-supporting films/sheets and molded articles.

The resulting phosphorus content in threads and fibers produced from flame-retardant polymers is preferably 0.1%-18% by weight, more preferably 0.5%-15% by weight and in the case of self-supporting films/sheets 0.2%-15% by weight, preferably 0.9%-12% by weight.

Suitable polyesters are derived from dicarboxylic acids and their esters and diols and/or from hydroxycarboxylic acids or the corresponding lactones.

It is particularly preferable to use terephthalic acid and ethylene glycol, 1,3-propanediol and 1,3-butanediol.

Suitable polyesters include inter alia polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Preferred polyolefins are for example polymers of mono- and diolefins (e.g., ethylene, propylene, isobutylene, butene, 4-methylpentene, isoprene, butadiene, styrene), e.g., polypropylene, polyisobutylene, polybut-1-ene, poly-4-methylpent-1-ene, polystyrene, poly(p-methylstyrene) and/or poly(alpha-methylstyrene), polyisoprene or polybutadiene, and polyethylene (optionally crosslinked), e.g., high density polyethylene (HDPE), high density and high molecular weight polyethylene (HDPE-HMW), high density and ultra high molecular weight polyethylene (HDPE-UHMW), medium density polyethylene (HMDPE), low density polyethylene (LDPE), linear low density polyethylene (LLDPE), very low density polyethylene (VLDPE), branched low density polyethylene (BLDPE), also polymers of cycloolefins, for example of cyclopentene or norbornene.

The aforementioned polyolefins, more particularly polyethylenes and polypropylenes, are preferably produced according to the prior art for example by free-radical polymerization (normally at high pressure and high temperatures) or catalytic polymerization by means of transition metal catalysts.

Preferred polymers further include blends of the polyolefins listed above, for example polypropylene with polyisobutylene, polyethylene with polyisobutylene, polypropylene with polyethylene (e.g., PP/HDPE/LDPE) and mixtures of various polyethylene types (e.g., LDPE/HDPE).

Preferred polymers further include copolymers of mono- and diolefins with each other and of mono- and diolefins with other vinylic monomers, for example ethylene-propylene copolymers; LLDPE, VLDPE and blends thereof with LDPE; propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers, copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another, polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene, also graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are also known for example as ABS, MBS, ASA or AES polymers; also their copolymers with carbon monoxide or ethylene-acrylic acid copolymers and their salts (ionomers) and also terpolymers of ethylene with propylene and a diene such as, for example, hexadiene, dicyclopentadiene or ethylidene-norbornene; and blends of such copolymers with each other and/or the polymers mentioned above, for example polypropylene-ethylene-propylene copolymer, LDPE-ethylene-vinyl acetate copolymer, LDPE-ethylene-acrylic acid copolymer, LLDPE-ethylene-vinyl acetate copolymer, LLDPE-ethylene-acrylic acid copolymer, and alternating or random polyalkylene-carbon monoxide copolymers and blends thereof with other polymers, such as polyamides for example.

The polymers preferably comprise polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7, 7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont; Durethan® B 29, from Bayer and Grillamid®, from Ems Chemie.

Also suitable are aromatic polyamides proceeding from m-xylene, diamine and adipic acid; polyamides produced from hexamethylenediamine and iso- and/or terephthalic acid and optionally an elastomer as modifier, for example poly-2, 4,4-trimethylhexamethyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The monoallyl-functionalized dialkylphosphinic acid/ester/salts produced according to one or more of claims 1 to 11 are preferably used in molding materials further used for producing polymeric molded articles.

It is particularly preferable for the flame-retardant molding material to contain from 5% to 30% by weight of monoallyl-functionalized dialkylphosphinic acids, salts or esters produced according to one or more of claims 1 to 11, from 5% to 90% by weight of polymer or mixtures thereof, from 5% to 40% by weight of additives and 5% to 40% by weight of filler, wherein the sum total of the components is always 100% by weight.

The present invention also provides flame retardants containing monoallyl-functionalized dialkylphosphinic acids, salts or esters produced according to one or more of claims 1 to 11.

The present invention also provides polymeric molding materials and also polymeric molded articles, films, threads and fibers containing the monoallyl-functionalized dialkylphosphinic acid salts of the metals Mg, Ca, Al, Zn, Ti, Sn, Zr, Ce or Fe produced according to the present invention.

More particularly, the present invention provides for the use of the monoallyl-functionalized dialkylphosphinic acid salts, produced in accordance with the present invention, as flame retardants for thermoplastic polymers such as polyesters, polystyrene or polyamide and for thermoset polymers such as unsaturated polyester resins, epoxy resins, polyurethanes or acrylates.

More particularly, the present invention provides for the use of monoallyl-functionalized dialkylphosphinic acid salts, produced in accordance with the present invention, as an intermediate in the manufacture of flame retardants for thermoplastic polymers such as polyesters, polystyrene or polyamide and for thermoset polymers such as unsaturated polyester resins, epoxy resins, polyurethanes or acrylates.

The examples which follow illustrate the invention.

Production, processing and testing of flame-retardant polymeric molding materials and flame-retardant polymeric molded articles.

The flame-retardant components are mixed with the polymeric pellets and any additives and incorporated on a twin-screw extruder (Leistritz LSM® 30/34) at temperatures of 230 to 260° C. (glassfiber-reinforced PBT) or of 260 to 280° C. (glassfiber-reinforced PA 66). The homogenized polymeric strand was hauled off, water bath cooled and then pelletized.

After sufficient drying, the molding materials were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens 1.5 mm in thickness.

The UL 94 fire classifications are as follows:
V-0: Afterflame time never longer than 10 sec, total of afterflame times for 10 flame applications not more than 50 sec, no flaming drops, no complete consumption of the specimen, afterglow time for specimens never longer than 30 sec after end of flame application.
V-1: Afterflame time never longer than 30 sec after end of flame application, total of afterflame time for 10 flame applications not more than 250 sec, afterglow time for specimens never longer than 60 sec after end of flame application, other criteria as for V-0
V-2: Cotton indicator ignited by flaming drops, other criteria as for V-1
Not classifiable (ncl): does not comply with fire classification V-2.

Some investigated specimens were also tested for their LOI value. The LOI (Limiting Oxygen Index) value is determined according to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| LOI | 23 | flammable |
| LOI | 24-28 | potentially flammable |
| LOI | 29-35 | flame resistant |
| LOI | >36 | particularly flame-resistant |

Chemicals and Abbreviations Used
VE water completely ion-free water
AIBN azobis(isobutyronitrile), (from WAKO Chemicals GmbH)
THF tetrahydrofuran
WakoV65 2,2'-azobis(2,4-dimethylvaleronitrile), (from WAKO Chemicals GmbH)
Deloxan® THP II metal scavenger (from Evonik Industries AG)
Palatal® A 400-01 unsaturated polyester resin (from BASF)
Butanox M 50 methylethyl ketone peroxide (from Akzo Chemie GmbH)
NL-49 P cobalt accelerant (from Akzo Chemie GmbH)

EXAMPLE 1

At room temperature, a three-neck flask equipped with stirrer and high-performance condenser is initially charged with 188 g of water and this initial charge is devolatilized by stirring and passing nitrogen through it. Then, under nitrogen, 0.2 mg of palladium(II) sulfate and 2.3 mg of tris(3-sulfophenyl)phosphine trisodium salt are added, the mixture is stirred, and then 66 g of phosphinic acid in 66 g of water are added. The reaction solution is transferred to a 2 l Büchi reactor and charged with ethylene under superatmospheric pressure while stirring and the reaction mixture is heated to 80° C. After 28 g of ethylene has been taken up, the system is cooled down and free ethylene is discharged. The reaction mixture is freed of solvent on a rotary evaporator. The residue is admixed with 100 g of VE water and at room temperature stirred under nitrogen, then filtered and the filtrate is extracted with toluene, thereafter freed of solvent on a rotary evaporator and the resulting ethylphosphonous acid is collected. Yield: 92 g (98% of theory) of ethylphosphonous acid.

EXAMPLE 2

Example 1 is repeated with 99 g of phosphinic acid, 396 g of butanol, 42 g of ethylene, 6.9 mg of tris(dibenzylideneacetone)dipalladium, 9.5 mg of 4,5-bis(diphenylphosphino)-9,9-dimethylxanthene, followed by purification over a column charged with Deloxan® THP II and the further addition of n-butanol. At a reaction temperature of 80-110° C., the water formed is removed by azeotropic distillation. The product is purified by distillation at reduced pressure. Yield: 189 g (84% of theory) of butyl ethylphosphonite.

EXAMPLE 3

Example 1 is repeated with 198 g of phosphinic acid, 198 g of water, 84 g of ethylene, 6.1 mg of palladium(II) sulfate, 25.8 mg of 9,9-dimethyl-4,5-bis(diphenylphosphino)-2,7-sulfonatoxanthene disodium salt, followed by purification over a column charged with Deloxan® THP II and the further addition of n-butanol. At a reaction temperature of 80-110° C., the water formed is removed by azeotropic distillation. The product is purified by distillation at reduced pressure. Yield: 374 g (83% of theory) of butyl ethylphosphonite.

EXAMPLE 4

A 500 ml five-neck flask equipped with gas inlet tube, thermometer, high-performance stirrer and reflux condenser with gas incineration is charged with 94 g (1 mol) of ethylphosphonous acid (produced as in Example 1). Ethylene oxide is introduced at room temperature. A reaction temperature of 70° C. is set with cooling, followed by further reaction at 80° C. for one hour. The ethylene oxide takeup is 65.7 g. The acid number of the product is less than 1 mg KOH/g. Yield: 129 g (94% of theory) of 2-hydroxyethyl ethylphosphonite as colorless, water-clear product.

EXAMPLE 5

At room temperature, a three-neck flask equipped with stirrer and high-performance condenser is initially charged with 400 g of ethanol and this initial charge is devolatilized by stirring and passing nitrogen through it. Then, under nitrogen, 1.35 g (6 mmol) of palladium acetate and 4.72 g (18 mmol) of triphenylphosphine are added and stirred in, then 30 g (0.2 mol) of butyl ethylphosphonite (produced as in Example 2) and 26.3 g (0.26 mol) of triethylamine are added and the reaction mixture is heated to 80° C. Thereafter, 26.0 g (0.26 mol) of allyl acetate are added dropwise. After a reaction time of 5 hours, the reaction solution is passed through a column charged with Deloxan® THP II for purification and the solvent is removed in vacuo. The product (butyl ethylpropenylphosphinate) is purified by column chromatography. This gives 21.3 g (56% of theory) of butyl ethylpropenylphosphinate as colorless oil.

EXAMPLE 6

At room temperature, a three-neck flask equipped with stirrer and high-performance condenser is initially charged with 400 g of toluene and this initial charge is devolatilized by stirring and passing nitrogen through it. Then, under nitrogen, 30 g (0.2 mol) of butyl ethylphosphonite (produced as in Example 2) and 36.5 g (0.24 mol) of 1,8-diazabicyclo[5.4.0]undec-7-ene are added and 29.0 g (0.24 mol) of allyl bromide are added dropwise. After a reaction time of 5 hours, the reaction solution is passed through a column charged with Deloxan® THP II for purification and the solvent is removed in vacuo. The product (butyl ethylpropenylphosphinate) is purified by column chromatography. This gives 4.9 g (13% of theory) of butyl ethylpropenylphosphinate as colorless oil.

EXAMPLE 7

At room temperature, a three-neck flask equipped with stirrer and high-performance condenser is initially charged with 400 g of toluene and this initial charge is devolatilized by stirring and passing nitrogen through it. Then, under nitrogen, 3.27 g (5 mmol) of bis(triphenylphosphine)nickel dichloride and 30 g (0.2 mol) of butyl ethylphosphonite (produced as in Example 3) and 36.5 g (0.24 mol) of 1,8-diazabicyclo[5.4.0]undec-7-ene are added, and 29.0 g (0.24 mol) of allyl bromide are added dropwise. Following a reaction time of 5 hours, the reaction solution is passed through a column charged with Deloxan® THP II for purification and the solvent is removed in vacuo. The product (butyl ethylpropenylphosphinate) is purified by column chromatography. Yield: 34.3 g (90% of theory) of butyl ethylpropenylphosphinate as colorless oil.

EXAMPLE 8

At room temperature, a three-neck flask equipped with stirrer and high-performance condenser is initially charged with 400 g of ethanol and this initial charge is devolatilized by stirring and passing nitrogen through it. Then, under nitrogen, 30 g (0.2 mol) of butyl ethylphosphonite (produced as in Example 3) are added, followed by the dropwise addition of initially 14.5 g (0.25 mol) of sodium ethoxide in ethanol and thereafter 19.1 g (0.25 mol) of allyl chloride. Following a reaction time of 5 hours, the reaction solution is passed for purification through a column charged with Deloxan® THP II and the solvent is removed in vacuo. The product (butyl ethylpropenylphosphinate) is purified by column chromatography to obtain 9.9 g (26% of theory) of butyl ethylpropenylphosphinate as colorless oil.

EXAMPLE 9

At room temperature, a three-neck flask equipped with stirrer and high-performance condenser is initially charged with 400 g of ethanol and this initial charge is devolatilized by stirring and passing nitrogen through it. Then, under nitrogen, 3.27 g (5 mmol) of bis(triphenylphosphine)nickel dichloride and 30 g (0.2 mol) of butyl ethylphosphonite (produced as in Example 2) are added followed by the dropwise addition of initially 14.5 g (0.25 mol) of sodium ethoxide in ethanol and thereafter 19.1 g (0.25 mol) of allyl chloride. Following a reaction time of 5 hours, the reaction solution is passed for purification through a column charged with Deloxan® THP II and the solvent is removed in vacuo. The product is purified by column chromatography to obtain 25.1 g (66% of theory) of butyl ethylpropenylphosphinate as colorless oil.

EXAMPLE 10

At room temperature, a three-neck flask equipped with stirrer and high-performance condenser is initially charged with 400 g of toluene and this initial charge is devolatilized by stirring and passing nitrogen through it. Then, under nitrogen, 6.65 g (6 mmol) of tetrakis(triphenylphosphine)nickel and 30 g (0.2 mol) of butyl ethylphosphonite (produced as in Example 2) and 30.4 g (0.2 mol) of 1,8-diazabicyclo[5.4.0]undec-7-ene are added followed by the dropwise addition of 20.9 g (0.2 mol) of 1-chloro-3-methyl-2-butene. Following a reaction time of 5 hours, the reaction solution is passed for purification through a column charged with Deloxan® THP Hand the solvent is removed in vacuo. The product is purified by column chromatography to obtain 33.1 g (76% of theory) of butyl ethyl(3-methyl-2-butenyl)phosphinate as colorless oil.

EXAMPLE 11

To 570 g (3.0 mol) of butyl ethylpropenylphosphinate (produced as in Example 6) are added 248 g (4 mol) of ethylene glycol and 0.4 g of potassium titanyl oxalate followed by stirring at 100° C. for 2 h. Volatiles are distilled off by gradual evacuation to leave 506 g (98% of theory) of 2-hydroxyethyl ethylpropenyl-phosphinate.

EXAMPLE 12

A stirred apparatus is initially charged with 150 g of butanol, 65 g of water, 150 g (3.75 mol) of sodium hydroxide and 237.5 g (1.25 mol) of butyl ethylpropenylphosphinate (produced as in Example 5). The efficiently stirred mixture was heated to about 80° C. and reacted at that temperature for about 8 hours. Then, 250 ml of water were added and the butanol was removed from the reaction mixture by distillation. Following the addition of a further 500 ml of water, the mixture is neutralized by addition of about 184 g (1.88 mol) of concentrated sulfuric acid. The water is then distilled off in vacuo. The residue is taken up in tetrahydrofuran and extracted. The solvent is removed in vacuo to obtain 266 g (99% of theory) of ethylpropenylphosphinic acid as an oil.

EXAMPLE 13

804 g (6 mol) of ethylpropenylphosphinic acid (produced as in Example 12) are dissolved in 860 g of water and initially charged into a 5 l five-neck flask equipped with thermometer, reflux condenser, high-performance stirrer and dropping funnel and neutralized with about 480 g (6 mol) of 50% sodium hydroxide solution. A mixture of 1291 g of a 46% aqueous solution of $Al_2(SO_4)_3 \cdot 14\,H_2O$ is added at 85° C. The solid material obtained is subsequently filtered off, washed with hot water and dried at 130° C. in vacuo. Yield: 801 g (94% of theory) of ethylpropenylphosphinic acid aluminum(III) salt as colorless salt.

EXAMPLE 14

134 g (1 mol) of ethylpropenylphosphinic acid (produced as in Example 12) and 85 g of titanium tetrabutoxide are refluxed in 500 ml of toluene for 40 hours. The resulting butanol is distilled off from time to time with proportions of toluene. The solution formed is subsequently freed of solvent to leave 133 g (92% of theory) of ethylpropenylphosphinic acid titanium salt.

EXAMPLE 15

0.5 part of NL-49 P and 55 parts of butyl ethylpropenylphosphinate (produced as in Example 9) are mixed. After homogenization, the curing is started by adding 2 parts of Butanox M-50 to obtain a polymer having a phosphorus content of 15.6% by weight.

EXAMPLE 16

35 parts of styrene are mixed with 0.5 part of NL-49 P, 55 parts of butyl ethylvinyl-phosphinate (produced as in Example 7) are added. After homogenization, the curing is started by adding 2 parts of Butanox M-50 to obtain a copolymer having a phosphorus content of 9.7% by weight. The LOI is 35, that of untreated styrene is 19.

EXAMPLE 17

100 parts of Palatal® A 400-01 unsaturated polyester resin are mixed with 0.5 part of NL-49 P, 55 parts of butyl ethyl-propenylphosphinate (produced as in Example 5) are added and, after homogenization, the curing is started by adding 2 parts of Butanox M-50.

Two layers of continuous glass textile mat having a basis weight of 450 g/m² are inserted within a heated press, on a Hostaphan® release film and a steel frame. About half of the resin is uniformly distributed. Thereafter, a further glass mat is added, and then the remaining resin is distributed, the laminate is covered with a release film, and a pressed plaque of thickness 4 mm is produced at a temperature of 50° C. over a period of one hour, using a pressure of 10 bar. The laminate obtained has a phosphorus content of 5.7% by weight. A UL-94 classification of V-0 was determined. The LOI is 34, that of untreated laminate is 21.

EXAMPLE 18

A mixture of 50% by weight of polybutylene terephthalate, 20% by weight of ethylpropenylphosphinic acid aluminium (III) salt (produced as in Example 13) and 30% by weight of glass fibers are compounded on a twin-screw extruder (Leistritz LSM 30/34) at temperatures of 230 to 260° C. to form a polymeric molding material. The homogenized polymeric strand was hauled off, water bath cooled and then pelletized. After drying, the molding materials are processed on an injection molding machine (Aarburg Allrounder) at 240 to 270° C. to form polymeric molded articles which achieved a UL-94 classification of V-0.

EXAMPLE 19

A mixture of 53% by weight of nylon-6,6, 30% by weight of glass fibers, 17% by weight of ethylpropenylphosphinic acid titanium salt (produced as in Example 14) are compounded on a twin-screw extruder (Leistritz LSM 30/34) to form polymeric molding materials. The homogenized polymeric strand was hauled off, water bath cooled and then pelletized. After drying, the molding materials are processed on an injection molding machine (Aarburg Allrounder) at 260 to 290° C. to form polymeric molded articles which achieved a UL-94 classification of V-0.

What is claimed is:
1. A method for producing monoallyl-functionalized dialkylphosphinic acids, esters or salts with allylic compounds, comprising the steps of
a) reacting a phosphinic acid source (I)

with one or more olefins (IV)

in the presence of a catalyst A to form an alkylphosphonous acid, salt or ester (II)

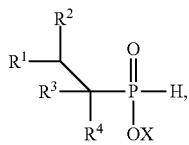
(II)

b) reacting the alkylphosphonous acid, salt or ester (II) with one or more allylic compounds of the formula (V)

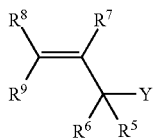
(V)

in the presence of a catalyst B and a base to form a monoallyl-functionalized dialkylphosphinic acid derivative (III)

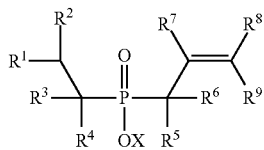
(III)

where $R^1$, $R^2$, $R^3$, $R^4$, $R^5$, $R^6$, $R^7$, $R^8$, $R^9$ are identical or different and are each independently H, $C_1$-$C_{18}$-alkyl, $C_6$-$C_{18}$-aryl, $C_6$-$C_1$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, (CH$_2$)$_m$OH, (CH$_2$)$_m$NH$_2$, (CH$_2$)$_m$NCS, (CH$_2$)$_m$NC(S)NH$_2$, (CH$_2$)$_m$SH, (CH$_2$)$_m$S-2-thiazoline, (CH$_2$)$_m$SiMe$_3$, C(O)R$^{10}$, (CH$_2$)$_m$C(O)R$^{10}$, CH=CHR$^{10}$ or CH=CH—C(O)R$^{10}$ and where $R^{10}$ is $C_1$-$C_8$-alkyl or $C_6$-$C_{18}$-aryl and m is an integer from 0 to 10 and X is H, $C_1$-$C_{18}$-alkyl, $C_6$-$C_{18}$-aryl, $C_6$-$C_{18}$-aralkyl, $C_6$-$C_{18}$-alkylaryl, (CH$_2$)$_k$OH, CH$_2$—CHOH—CH$_2$OH, (CH$_2$)$_k$O(CH$_2$)$_k$H, (CH$_2$)$_k$—CH(OH)—(CH$_2$)$_k$H, (CH$_2$—CH$_2$O)$_k$H, (CH$_2$—C[CH$_3$]HO)$_k$H, (CH$_2$—C[CH$_3$]HO)$_k$(CH$_2$—CH$_2$O)$_k$H (CH$_2$—CH$_2$O)$_k$(CH$_2$—C[CH$_3$]HO)H, (CH$_2$—CH$_2$O)$_k$-alkyl, (CH$_2$—C[CH$_3$]HO)$_k$-alkyl, (CH$_2$—C[CH$_3$]HO)$_k$(CH$_2$—CH$_2$O)$_k$-alkyl, (CH$_2$—CH$_2$O)$_k$(CH$_2$—C[CH$_3$]HO)O-alkyl, (CH$_2$)$_k$—CH=CH(CH$_2$)$_k$H, (CH$_2$)$_k$NH$_2$, (CH$_2$)$_k$N[(CH$_2$)$_k$H]$_2$ or a combination thereof, where k is an integer from 0 to 10, Mg, Ca, Al, Sb, Sn, Ge, Ti, Fe, Zr, Zn, Ce, Bi, Sr, Mn, Cu, Ni, Li, Na, K, H a protonated nitrogen base or a combination thereof and Y is a halogen or acetate and the catalysts A and B are transition metals, transition metal compounds, catalyst systems composed of a transition metal, transition metal compound or combination thereof and at least one ligand or a combination thereof.

2. The method according to claim 1 wherein the monoallyl-functionalized dialkylphosphinic acid, its salt or ester (III) obtained after step b) is subsequently reacted in a step c) with metal compounds of Mg, Ca, Al, Sb, Sn, Ge, Ti, Fe, Zr, Zn, Ce, Bi, Sr, Mn, Li, Na, K a protonated nitrogen base or a combination thereof to form the corresponding monoallyl-functionalized dialkylphosphinic acid salts (III) of these metals, of a nitrogen compound or a combination thereof.

3. The method according to claim 1 wherein the alkylphosphonous acid, salt or ester (II) obtained after step a), the monoallyl-functionalized dialkylphosphinic acid, salt or ester (III) obtained after step b), the reaction solution thereof or a combination thereof are esterified with an alkylene oxide or an alcohol M-OH, M'-OH or a combination thereof, and the alkylphosphonous ester (II), monoallyl-functionalized dialkylphosphinic ester (III) or a combination thereof are subjected to the reaction steps b) or c).

4. The method according to claim 1, wherein the groups $C_6$-$C_{18}$-aryl, $C_6$-$C_{18}$-aralkyl and $C_6$-$C_{18}$-alkylaryl are substituted with SO$_3$X$_2$, —C(O)CH$_3$, OH, CH$_2$OH, CH$_3$SO$_3$X$_2$, PO$_3$X$_2$, NH$_2$, NO$_2$, OCH$_3$, SHOC(O)CH$_3$ or a combination thereof.

5. The method according to claim 1, wherein $R^1$, $R^2$, $R^3$, $R^4$, $R^5$, $R^6$, $R^7$, $R^8$, $R^9$ are identical or different and are each independently H, methyl, ethyl, n-propyl, isopropyl, n-butyl, isobutyl, tert-butyl or phenyl.

6. The method according to claim 1, wherein X is H, Ca, Mg, Al, Zn, Ti, Fe, Ce, methyl, ethyl, n-propyl, isopropyl, n-butyl, isobutyl, tert-butyl, phenyl, ethylene glycol, propyl glycol, butyl glycol, pentyl glycol, hexyl glycol, allyl, glycerol or a combination thereof.

7. The method according to claim 1, wherein the transition metals, transition metal compounds or a combination thereof are from the seventh or eighth transition groups.

8. The method according to claim 1, wherein the transition metals, transition metal compounds or combination thereof are rhodium, nickel, palladium, platinum or ruthenium.

9. The method according to claim 1, wherein the one or more allylic compounds are 3-chloro-1-propene, 3-chloro-2-methyl-1-propene, 3-chloro-1-phenyl-1-propene, 1-chloro-2-butene, 1-chloro-3-methyl-2-butene, 3-bromo-1-propene, 3-bromo-2-methyl-1-propene, 3-bromo-1-phenyl-1-propene, 1-bromo-2-butene, 1-bromo-3-methyl-2-butene, allyl acetate, 2-methylallyl acetate or a combination thereof.

10. The method according to claim 1, wherein the base is selected from the group consisting of an alkali, alkaline earth metals, alkali metal hydrides, alkoxides, hydroxides, alkaline earth metal hydrides, alkoxides, hydroxides, amines, diamines and organolithium compounds.

11. The method according to claim 1, wherein the alcohol of the general formula M-OH is a linear or branched, saturated or an 4 unsaturated, monohydric organic alcohol having a carbon chain length of $C_1$-$C_{18}$ and the alcohol of the general formula M'-OH is a linear or branched, saturated or unsaturated polyhydric organic alcohol having a carbon chain length of $C_1$-$C_{18}$.

* * * * *